(12) United States Patent
Chuang et al.

(10) Patent No.: US 11,970,492 B2
(45) Date of Patent: Apr. 30, 2024

(54) 11-ARYLCINNOLINO[2,3-F] PHENANTHRIDINIUM SALTS AND METHOD FOR PRODUCING THE SAME

(71) Applicant: NATIONAL CHIAO TUNG UNIVERSITY, Hsinchu (TW)

(72) Inventors: Shih-Ching Chuang, Hsinchu (TW); Jayakumar Jayachandran, Hsinchu (TW)

(73) Assignee: NATIONAL CHIAO TUNG UNIVERSITY, Hsinchu (TW)

(*) Notice: Subject to any disclaimer, the term of this patent is extended or adjusted under 35 U.S.C. 154(b) by 646 days.

(21) Appl. No.: 17/161,992

(22) Filed: Jan. 29, 2021

(65) Prior Publication Data

US 2021/0147420 A1    May 20, 2021

Related U.S. Application Data

(62) Division of application No. 16/664,370, filed on Oct. 25, 2019, now Pat. No. 10,947,232.

(30) Foreign Application Priority Data

Aug. 30, 2019 (TW) ................. 108131307

(51) Int. Cl.
    *C07D 471/04*      (2006.01)
    *C07D 495/14*      (2006.01)

(52) U.S. Cl.
    CPC ......... *C07D 471/04* (2013.01); *C07D 495/14* (2013.01)

(58) Field of Classification Search
None
See application file for complete search history.

(56) References Cited

PUBLICATIONS

Jayakumar, Angewandte Chemie, International Edition, 2019, 59, 689-694 (Year: 2019).*
IUPAC Compendium of Chemical Terminology, entry A00464, 2014, doi:10.1351/goldbook.A00464, accessed Sep. 29, 2023 (Year: 2014).*
"Aryl groups", doi:10.1351/goldbook.A00464, 1995, accessed Feb. 10, 2024 (Year: 1995).*
"Heteroarenes", doi:10.1351/goldbook.H02791, 1995, accessed Feb. 10, 2024 (Year: 1995).*
Xu. Chemical Physics, 2003, 287, 317-333 (Year: 2003).

* cited by examiner

*Primary Examiner* — Noble E Jarrell
(74) *Attorney, Agent, or Firm* — Birch, Stewart, Kolasch & Birch, LLP (57) ABSTRACT

The present invention provides 11-arylcinnolino[2,3-f] phenanthridinium salt compounds and method for producing the same by highly regioselective synthesis of 11-phenylimino[2,3-f]phenanthridin-9-ium salts from 2-azobiaryls and alkenes under catalysis of palladium, through double oxidative C—H coupling of alkenes, to give the polycyclic cinnolinophenanthridinium salts in moderate yields. The reaction mechanism involves ortho C—H olefination of 2-azobiaryls by alkenes, intramolecular aza-Michael addition, β-hydride elimination, electrophilic palladation followed by intramolecular C—H activation and reductive elimination. The prepared quaternary ammonium salts are candidate materials for solution-processable OLED and bio-imaging materials.

2 Claims, 2 Drawing Sheets

11-ARYLCINNOLINO[2,3-F] PHENANTHRIDINIUM SALTS AND METHOD FOR PRODUCING THE SAME

CROSS-REFERENCE TO RELATED APPLICATIONS

This application is a Divisional of copending application Ser. No. 16/664,370, filed on Oct. 25, 2019, which claims priority under 35 U.S.C. § 119(a) to Application No. 108131307, filed in Taiwan on Aug. 30, 2019, all of which are hereby expressly incorporated by reference into the present application.

BACKGROUND

Technical Field

The invention relates to 11-arylcinnolino[2,3-f] phenanthridinium salt compounds and method for producing the same.

Related Art

Cinnolinium salts are receiving increasing attention due to their applications in organic optoelectronic materials, and specifically high molecular weight cinnolinium salts with good solubility in organic solvents have high potential. Nevertheless, traditional methods for the synthesis of cinnolinium salts are inefficient and costly, so there is room for improvement.

SUMMARY

The main object of the invention is to provide a 11-arylcinnolino[2,3-f]phenanthridinium salt compounds in higher yield and lower manufacturing cost.

Another object of the invention is to provide a method for producing the 11-arylcinnolino[2,3-f]phenanthridinium salt compounds in higher yield and lower manufacturing cost.

The 11-arylcinnolino[2,3-f]phenanthridinium salt compounds of the invention have the structure of the following formula (1):

formula (1)

wherein, $R^1$ is selected from hydrogen (H), deuterium (D), methyl (Me), isopropyl ($^i$Pr), phenyl (Ph), methoxy (OMe), oxytrifluoromethyl ($OCF_3$), trifluoromethyl ($CF_3$), fluorine (F), dimethylamino ($NMe_2$), and cyano (CN);

$R^2$ is selected from hydrogen (H), deuterium (D), methyl (Me), isopropyl ($^i$Pr), phenyl (Ph), methoxy (OMe), oxytrifluoromethyl ($OCF_3$), trifluoromethyl ($CF_3$), fluorine (F), dimethylamino ($NMe_2$), and cyano (CN);

R is selected from the group consisting of an ester ($CO_2R'$), an amide ($CONR'_2$), a ketone group ($COR'$), aryl (Ar), a nitrile (CN), a nitro group ($NO_2$), trifluoromethyl ($CF_3$), a phosphonate($P(=O)OR'_2$), a phosphine oxide ($P(=O)R'_2$), a sulfonyl group ($SOR'$), and a sulfur oxide ($SO_2R'$), and R' is selected from a group consisting of alkyl and aryl.

In an embodiment of the invention, the 11-arylcinnolino[2,3-f]phenanthridinium salt compounds have the structure of the following formula (A):

formula (A)

wherein, R is selected from the group consisting of methoxycarbonyl ($CO_2Me$), butoxycarbonyl ($CO_2Bu$), ethoxycarbonyl ($CO_2Et$), (benzyloxy)carbonyl ($CO_2Bn$), (cyclohexyloxy)carbonyl ($CO_2cyhex$), ((tetrahydrofuran-2-yl)methoxy)carbonyl ($CO_2furfuryl$), phenoxycarbonyl ($CO_2Ph$), and dimethylcarbamoyl ($CONMe_2$).

In an embodiment of the invention, the 11-arylcinnolino[2,3-f]phenanthridinium salt compounds have the structure of the following formula (A):

formula (A)

wherein, R is selected from the group consisting of acetyl (COMe) and phenyl (Ph).

In an embodiment of the invention, the 11-arylcinnolino[2,3-f]phenanthridinium salt compounds of claim 1 have the structure of the following formula (B):

formula (B)

wherein, R is selected from the group consisting of ((tetrahydrofuran-2-yl) methoxy)carbonyl (CO$_2$furfuryl) and dimethylcarbamoyl (CONMe$_2$).

In an embodiment of the invention, the 11-arylcinnolino[2,3-f]phenanthridinium salt compounds include 15-(((tetrahydrofuran-2-yl)methoxy)carbonyl)-7,14-dimethyl-11-phenylcinnolino[2,3-f]phenanthridin-9-ium tetrafluoroborate, and have the structure of the following formula (C):

formula (C)

wherein, R includes ((tetrahydrofuran-2-yl)methoxy)carbonyl (CO$_2$furfuryl).

In an embodiment of the invention, the 11-arylcinnolino[2,3-f]phenanthridinium salt compounds include 15-(butoxycarbonyl)-3-methyl-11-(m-tolyl)cinnolino[2,3-f]phenanthridin-9-ium tetrafluoroborate, and have the structure of the following formula (D):

formula (D)

wherein, R includes butoxycarbonyl (CO$_2$Bu), and R$^2$ includes methyl (Me).

In an embodiment of the invention, the 11-arylcinnolino[2,3-f]phenanthridinium salt compounds include 3-fluoro-11-(3-fluorophenyl)-15-(((tetrahydrofuran-2-yl)methoxy)carbonyl)cinnolino[2,3-f]phenanthridin-9-ium tetrafluoroborate, and have the structure of the following formula (E):

formula (E)

wherein, R includes ((tetrahydrofuran-2-yl)methoxy)carbonyl (CO$_2$furfuryl), and R$^2$ includes fluorine.

In an embodiment of the invention, the 11-arylcinnolino[2,3-f]phenanthridinium salt compounds of claim 1 include 15-(butoxycarbonyl)-4-chloro-11-(2-chlorophenyl) cinnolino[2,3-f]phenanthridin-9-ium tetrafluoroborate, and have the structure of the following formula (F):

formula (F)

In an embodiment of the invention, the 11-arylcinnolino[2,3-f]phenanthridinium salt compounds include 14-(((tetrahydrofuran-2-yl)methoxy)carbonyl)-10-(thiophen-2-yl)thieno[3',2':3,4]quinolino[1,2-b]cinnolin-8-ium tetrafluoroborate, and have the structure of the following formula (G):

formula (G)

Provided is a method for producing the 11-arylcinnolino[2,3-f]phenanthridinium salt compounds of the invention by the following equation, wherein, the 11-arylcinnolino[2,3-f]phenanthridinium salt compounds have the structure of the following formula (1):

formula (1)

$R^1$ is selected from hydrogen (H), deuterium (D), methyl (Me), isopropyl ($^i$Pr), phenyl (Ph), methoxy (OMe), oxytrifluoromethyl ($OCF_3$), trifluoromethyl ($CF_3$), fluorine (F), dimethylamino ($NMe_2$), and cyano (CN);

$R^2$ is selected from hydrogen (H), deuterium (D), methyl (Me), isopropyl ($^i$Pr), phenyl (Ph), methoxy (OMe), oxytrifluoromethyl ($OCF_3$), trifluoromethyl ($CF_3$), fluorine (F), dimethylamino ($NMe_2$), and cyano (CN);

R is selected from the group consisting of an ester ($CO_2R'$), an amide ($CONR'_2$), a ketone group (COR'), aryl (Ar), a nitrile (CN), a nitro group ($NO_2$), trifluoromethyl ($CF_3$), a phosphonate (P(=O)OR'$_2$), a phosphine oxide (P(=O)R'$_2$), a sulfonyl group (SOR'), and a sulfur oxide ($SO_2R'$), and R' is selected from a group consisting of alkyl and aryl.

In an embodiment, 2-azobiaryls are produced by the following equation, wherein the 2-azobiaryls have the structure of formula (2):

formula (2)

DETAILED DESCRIPTION

The 11-arylcinnolino[2,3-f]phenanthridinium salt compounds of the invention have the structure of the following formula (1):

formula (1)

wherein, $R^1$ is selected from hydrogen (H), deuterium (D), methyl (Me), isopropyl ($^i$Pr), phenyl (Ph), methoxy (OMe), oxytrifluoromethyl (OCF$_3$), trifluoromethyl (CF$_3$), fluorine (F), dimethylamino (NMe$_2$), and cyano (CN);

$R^2$ is selected from hydrogen (H), deuterium (D), methyl (Me), isopropyl ($^i$Pr), phenyl (Ph), methoxy (OMe), oxytrifluoromethyl (OCF$_3$), trifluoromethyl (CF$_3$), fluorine (F), dimethylamino (NMe$_2$), and cyano (CN);

R is selected from the group consisting of an ester (CO$_2$R'), an amide (CONR'$_2$), a ketone group (COR'), aryl (Ar), a nitrile (CN), a nitro group (NO$_2$), trifluoromethyl (CF$_3$), a phosphonate (P(=O)OR'$_2$), a phosphine oxide (P(=O)R'$_2$), a sulfonyl group (SOR'), and a sulfur oxide (SO$_2$R'), and R' is selected from a group consisting of alkyl and aryl.

In an embodiment, the 11-arylcinnolino[2,3-f]phenanthridinium salt compounds are produced by the following equation, wherein, the 11-arylcinnolino[2,3-f]phenanthridinium salt compounds have the structure of the following formula (1):

formula (1)

$R^1$ is selected from hydrogen (H), deuterium (D), methyl (Me), isopropyl ($^i$Pr), phenyl (Ph), methoxy (OMe), oxytrifluoromethyl (OCF$_3$), trifluoromethyl (CF$_3$), fluorine (F), dimethylamino (NMe$_2$), and cyano (CN);

$R^2$ is selected from hydrogen (H), deuterium (D), methyl (Me), isopropyl ($^i$Pr), phenyl (Ph), methoxy (OMe), oxytrifluoromethyl (OCF$_3$), trifluoromethyl (CF$_3$), fluorine (F), dimethylamino (NMe$_2$), and cyano (CN);

R is selected from the group consisting of an ester (CO$_2$R'), an amide (CONR'$_2$), a ketone group (COR'), aryl (Ar), a nitrile (CN), a nitro group (NO$_2$), trifluoromethyl (CF$_3$), a phosphonate (P(=O)OR'$_2$), a phosphine oxide (P(=O)R'$_2$), a sulfonyl group (SOR'), and a sulfur oxide (SO$_2$R'), and R' is selected from a group consisting of alkyl and aryl.

More specifically, in an embodiment, according to the following equation, 2a, 0.1 mmol -continued

Pd(OAc)$_2$ (0.01 mmol, 2.2 mg), Cu(OAc)$_2$ (0.3 mmol, 54.3 mg), and CuCl$_2$ (0.3 mmol, 40.4 mg) were added to a sealed test tube containing 2-azo-biaryls (2a, 0.1 mmol). Then, triflouroethanol (TFE, 2.0 mL) and butyl acrylate (3b, 0.2 mmol) were syringed to the mixture in sequence in the atmosphere. The mixture was heated to 100-120 degrees centigrade for 12-16 hours. The product mixture of the reaction was cooled to room temperature, and diluted with CH$_2$Cl$_2$ (10 mL); then, the solution was subject to vacuum concentration, and the residue was purified by silica gel column chromatography (Pet ether; EtOAc/MeOH (~5%)) to serve as an intermediate complex. Then, the intermediate complex was treated with AgBF$_4$ (2.5 eqiuv) in dichloromethane as a solvent, stirred at room temperature for 2-5 minutes, filtered by diatomaceous earth, and subjected to vacuum concentration to obtain a 15-(butoxycarbonyl)-11-phenylcinnolino[2,3-f] phenanthridin-9-ium tetrafluoroborate salt (4ab).

Wherein the property measurement results of the salt (4ab) are shown as follows: Red solid; m.p. 204-209° C.; 1H NMR (700 MHz, CDCl$_3$): δ 8.87 (d, J=8.4 Hz, 1H), 8.78 (d, J=8.4 Hz, 1H), 8.75 (d, J=7.7 Hz, 1H), 8.60 (d, J=8.4 Hz, 1H), 8.35-8.29 (m, 3H), 8.12 (t, J=7.7 Hz, 1H), 8.00 (t, J=7.7 Hz, 1H), 7.99-7.85 (m, 4H), 7.67-7.64 (m, 3H), 4.67 (t, J=11.2 Hz, 2H), 1.78-1.75 (m, 2H), 1.36-1.32 (m, 2H), 0.91 (t, J=7.7 Hz, 3 H); $^{13}$C NMR (175 MHz, CDCl$_3$): δ 164.7, 145.8, 142.4, 138.8, 137.8, 136.7, 135.6, 135.3, 134.9, 134.7, 132.8, 132.0, 131.3, 130.1, 129.8, 129.6, 128.8, 128.4, 126.7, 126.0, 124.0, 123.8, 123.2, 121.9, 121.5, 68.7, 29.9, 18.9, 13.5; $^{11}$B NMR (191 MHz, CDCl$_3$): δ −2.89; $^{19}$F NMR (563 MHz, CDCl$_3$): δ −153.52, −153.57 and secondary isotopic shift ($^{10}$B, $^{11}$B) of 0.05 ppm; HRMS (ESI$^+$) calcd for C$_{31}$H$_{25}$N$_2$O$_2{}^+$457.1911, found 457.1910; IR (KBr): 3085, 1675, 1581, 1056 (vs-F), 775 and 502 cm$^{-1}$.

In an embodiment, 2-azobiaryls are produced by the following equation,

More specifically, the substituted 2-amino-biaryls (1a, 2.00 mmol) were dissolved in toluene (15 mL) in a round-bottom flask, and then meta-chloroperoxybenzoic acid (516 mg, 3.00 mmol) was added in portions under nitrogen at 0 degrees centigrade. The reaction mixture was stirred at room temperature for 12-18 hours. Then, the crude product was purified by flash column chromatography (2% EtOAc in petroleum ether) to obtain the desirable product (2a) as orange solid in yield of 70%.

In a different embodiment, according to the following equation,

2a

5ab

Pd(OAc)$_2$ (0.01 mmol, 2.2 mg), Cu(OAc)$_2$ (0.3 mmol, 54.3 mg), and PivOH (0.3 mmol, 40.4 mg) were added to a sealed test tube containing 2-azo-biaryls (2a, 0.1 mmol). Then, triflouroethanol (TFE, 2.0 mL) and butyl acrylate (3b, 0.2 mmol) were syringed to the mixture in sequence in the atmosphere. The mixture was heated to 100-120 degrees centigrade for 12-16 hours. The product mixture of the reaction was cooled to room temperature, and diluted with CH$_2$Cl$_2$ (10 mL); then, the solution was subject to vacuum concentration, and the residue was purified by silica gel column chromatography (Pet ether; EtOAc/MeOH (~5%)) to serve as an intermediate complex. Then, the intermediate complex was treated with AgBF$_4$ (2.5 equiv) in dichloromethane as a solvent, stirred at room temperature for 2-5 minutes, filtered by diatomaceous earth, and subjected to vacuum concentration to obtain a 15-(butoxycarbonyl)-15-hydroxy-11-phenyl-15H-cinnolino[2,3-f] phenanthridin-9-ium-10 salt (5ab) with a required yield. Wherein the salt (5ab) was preferably stored in methanol at 5 degrees centigrade.

In other words, in a way similar to said equations, 2-azo-biaryls and butyl acrylate can react to form 11-arylcinnolino[2,3-f]phenanthridinium salts in the presence of Pd(OAc)$_2$ as a catalyst. Furthermore, a highly regioselective synthesis of 11-arylcinnolino[2,3-f]phenanthridin-9-ium salts from 2-azobiaryls and alkenes is catalyzed by palladium, through double oxidative C—H coupling of alkenes, giving polycyclic cinnolinium salts in moderate yields. The reaction mechanism involves ortho C—H olefination of 2-azobiaryls by alkenes, intramolecular aza-Michael addition, β-hydride elimination, electrophilic palladation followed by intramolecular C—H activation and reductive elimination. On the other hand, the resulted 11-arylcinnolino[2,3-f]phenanthridinium salt compounds have a high molecular weight, and a good solubility greater than 20 mg/ml in various organic solvents, including toluene, dichloromethane, chloroform, dichlorobenzene, 1,4-dioxane and tetrahydrofuran. In addition, the salts have high potential for the solution processing of an orange-red OLED material and bioimaging application. Traditional fluorescent orange-red materials all depend on transition metal-containing luminous bodies, and the transition metal-containing luminous bodies usually have lower internal quantum yield and a broader spectrum. Because a metal-free luminous body has higher solubility and quantum yield, recent development gradually focuses on the design and synthesis of a metal-free organic material. The organic material, usually having a functional group capable of pushing and pulling electrons to lead to electron transfer, appears as a narrow bandwidth orange-red organic light-emitting diode. Therefore, the 11-arylcinnolino[2,3-f]phenanthridin-9-ium salts can have high potential to serve as a solution-processed orange-red OLED material.

More specifically, in an embodiment of the invention, 11-arylcinnolino[2,3-f]phenanthridinium salt compounds have the structure of the following formula (A):

formula (A)

wherein, R is selected from the group consisting of methoxycarbonyl (CO$_2$Me), butoxycarbonyl (CO$_2$Bu), ethoxycarbonyl (CO$_2$Et), (benzyloxy)carbonyl (CO$_2$Bn), (cyclohexyloxy)carbonyl (CO$_2$cyhex), ((tetrahydrofuran-2-yl)methoxy)carbonyl (CO$_2$furfuryl), phenoxycarbonyl (CO$_2$Ph), and dimethylcarbamoyl (CONMe$_2$). Furthermore, the 11-arylcinnolino[2,3-f]phenanthridin-9-ium salts are included in Table 1 below.

TABLE 1

| No. | The names of 11-arylcinnolino[2,3-f]phenanthridinium salt compounds |
|---|---|
| 4aa | 15-(Methoxycarbonyl)-11-phenylcinnolino[2,3-f]phenanthridin-9-ium tetrafluoroborate |
| 4ab | 15-(Butoxycarbonyl)-11-phenylcinnolino[2,3-f]phenanthridin-9-ium tetrafluoroborate |
| 4ac | 15-(Ethoxycarbonyl)-11-phenylcinnolino[2,3-f]phenanthridin-9-ium tetrafluoroborate |
| 4ad | 15-((Benzyloxy)carbonyl)-11-phenylcinnolino[2,3-f]phenanthridin-9-ium tetrafluoroborate |
| 4ae | 15-((Cyclohexyloxy)carbonyl)-11-phenylcinnolino[2,3-f]phenanthridin-9-ium tetrafluoroborate |
| 4af | 11-Phenyl-15-(((tetrahydrofuran-2-yl)methoxy)carbonyl)cinnolino[2,3-f]phenanthridin-9-ium tetrafluoroborate |
| 4ag | 15-(Phenoxycarbonyl)-11-phenylcinnolino[2,3-f]phenanthridin-9-ium tetrafluoroborate |
| 4ah | 15-(Dimethylcarbamoyl)-11-phenylcinnolino[2,3-f]phenanthridin-9-ium tetrafluoroborate |

In a different embodiment of the invention, the 11-aryl-cinnolino[2,3-f]phenanthridinium salt compounds have the structure of the following formula (A):

formula (A)

wherein, R is selected from the group consisting of acetyl (COMe) and phenyl (Ph).

Furthermore, the 11-arylcinnolino[2,3-f]phenanthridin-9-ium salts are included in Table 2 below.

TABLE 2

| No. | The names of 11-arylcinnolino[2,3-f]phenanthridinium salt compounds |
|---|---|
| 4ai | 15-Acetyl-11-phenylcinnolino[2,3-f]phenanthridin-9-ium tetrafluoroborate |
| 4aj | 11,15-Diphenylcinnolino[2,3-f]phenanthridin-9-ium tetrafluoroborate |

In a different embodiment, the 11-arylcinnolino[2,3-f]phenanthridinium salt compounds of claim 1 have the structure of the following formula (B):

formula (B)

wherein, R is selected from the group consisting of ((tetrahydrofuran-2-yl)methoxy)carbonyl ($CO_2$furfuryl) and dimethylcarbamoyl ($CONMe_2$).

Furthermore, the 11-arylcinnolino[2,3-f]phenanthridin-9-ium salts are included in Table 3 below.

TABLE 3

| No. | The names of 11-arylcinnolino[2,3-f]phenanthridinium salt compounds |
|---|---|
| 4bf | 7,14-Dimethyl-11-phenyl-15-(((tetrahydrofuran-2-yl)methoxy)carbonyl)cinnolino[2,3-f]phenanthridin-9-ium tetrafluoroborate |
| 4bh | 15-(Dimethylcarbamoyl)-7,14-dimethyl-11-phenylcinnolino[2,3-f]phenanthridin-9-ium tetrafluoroborate |

In a different embodiment of the invention, the 11-aryl-cinnolino[2,3-f] phenanthridinium salt compounds include 15-(dimethylcarbamoyl)-7,14-dimethyl-11-phenylcinnolino [2,3-f]phenanthridin-9-ium tetrafluoroborate, and have the structure of the following formula (C):

formula (C)

Furthermore, the 11-arylcinnolino[2,3-f]phenanthridin-9-ium salts are included in Table 4 below.

TABLE 4

| No. | The names of 11-arylcinnolino[2,3-f]phenanthridinium salt compounds |
|---|---|
| 4cf | 6,13-Dimethyl-11-phenyl-15-(((tetrahydrofuran-2-yl)methoxy)carbonyl)cinnolino[2,3-f]phenanthridin-9-ium tetrafluoroborate |

In a different embodiment of the invention, the 11-aryl-cinnolino[2,3-f] phenanthridinium salt compounds include 15-(butoxycarbonyl)-3-methyl-11-(m-tolyl)cinnolino[2,3-f] phenanthridin-9-ium tetrafluoroborate, and have the structure of the following formula (D):

formula (D)

wherein, R includes butoxycarbonyl ($CO_2Bu$), and $R^2$ includes methyl (Me).

Furthermore, the 11-arylcinnolino[2,3-f]phenanthridin-9-ium salts are included in Table 5 below.

TABLE 5

| No. | The names of 11-arylcinnolino[2,3-f]phenanthridinium salt compounds |
|---|---|
| 4db | 15-(Butoxycarbonyl)-3-methyl-11-(m-tolyl)cinnolino [2,3-f]phenanthridin-9-ium tetrafluoroborate |

In a different embodiment of the invention, the 11-aryl-cinnolino[2,3-f]phenanthridinium salt compounds include 3-fluoro-11-(3-fluorophenyl)-15-(((tetrahydrofuran-2-yl) methoxy)carbonyl)cinnolino[2,3-f]phenanthridin-9-ium tetrafluoroborate, and have the structure of the following formula (E):

formula (E)

wherein, R includes ((tetrahydrofuran-2-yl)methoxy)carbonyl (CO$_2$furfuryl), and R$^2$ includes fluorine.

Furthermore, the 11-arylcinnolino[2,3-f]phenanthridinium salt compounds are included in Table 6 below.

TABLE 6

| No. | The names of 11-arylcinnolino[2,3-f]phenanthridinium salt compounds |
|---|---|
| 4ef | 3-fluoro-11-(3-fluorophenyl)-15-(((tetrahydrofuran-2-yl)methoxy)carbonyl)cinnolino[2,3-f]phenanthridin-9-ium tetrafluoroborate |

In a different embodiment of the invention, the 11-arylcinnolino[2,3-f]phenanthridinium salt compounds of claim 1 include 15-(butoxycarbonyl)-4-chloro-11-(2-chlorophenyl)cinnolino[2,3-f]phenanthridin-9-ium tetrafluoroborate, and have the structure of the following formula (F):

formula (F)

Furthermore, the 11-arylcinnolino[2,3-f]phenanthridinium salt compounds are included in Table 7 below.

TABLE 7

| No. | The names of 11-arylcinnolino[2,3-f]phenanthridinium salts |
|---|---|
| 4fb | 15-(butoxycarbonyl)-4-chloro-11-(2-chlorophenyl)cinnolino[2,3-f]phenanthridin-9-ium tetrafluoroborate |

In a different embodiment of the invention, the 11-arylcinnolino[2,3-f]phenanthridinium salt compounds include 14-(((tetrahydrofuran-2-yl)methoxy)carbonyl)-10-(thiophen-2-yl)thieno[3',2':3,4]quinolino[1,2-b]cinnolin-8-ium tetrafluoroborate, and have the structure of the following formula (G):

formula (G)

Furthermore, the 11-arylcinnolino[2,3-f]phenanthridinium salts are included in Table 8 below.

TABLE 8

| No. | The names of 11-arylcinnolino[2,3-f]phenanthridinium salts |
|---|---|
| 4gf | 14-(((tetrahydrofuran-2-yl)methoxy)carbonyl)-10-(thiophen-2-yl)thieno[3',2':3,4]quinolino[1,2-b]cinnolin-8-ium tetrafluoroborate |

Figure 1:
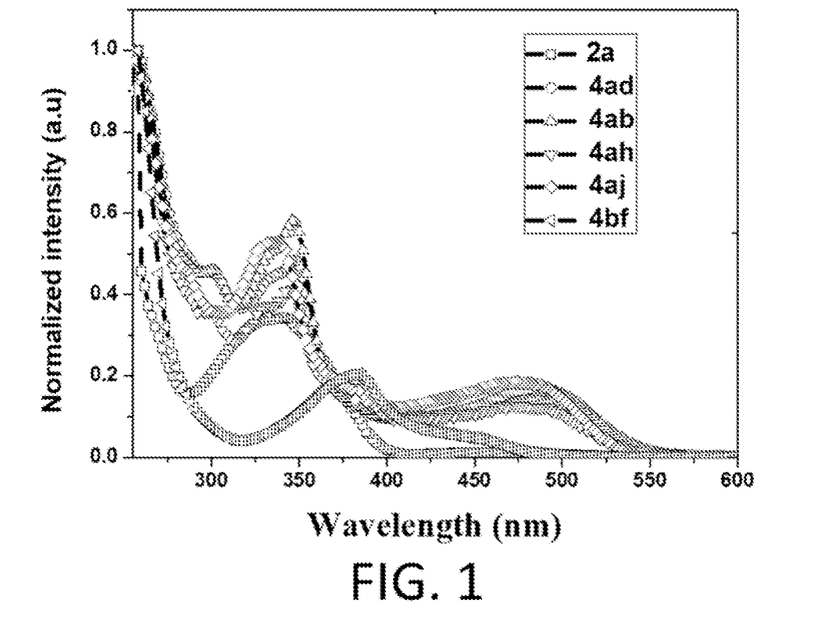
FIG. 1: Light absorption testing results.
Figure 2:
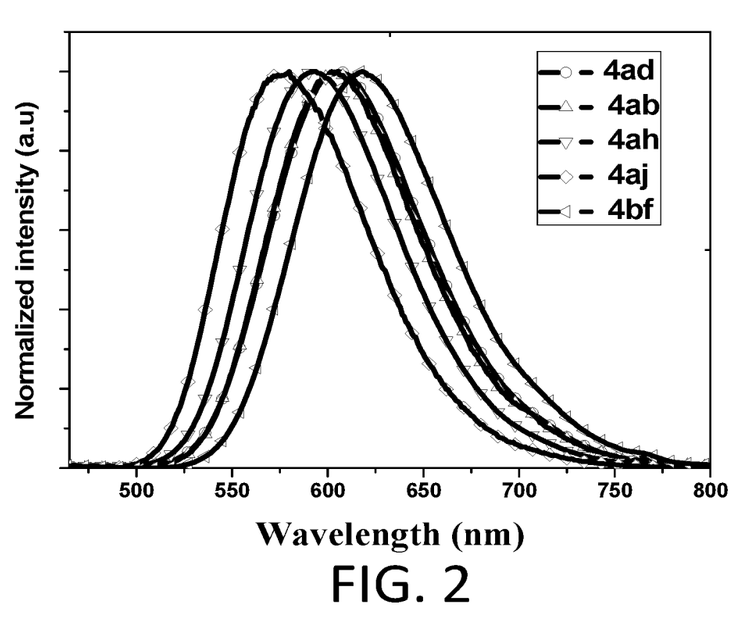
FIG. 2: Fluorescence testing results.

The absorption test and the fluorescence test (1.0×10$^{-5}$ M, excitation wavelength: 360 nm, in dichloromethane) were performed on the compounds 2a, 4ab, 4ad, 4ah, 4aj, and 4bf, and the results were shown in FIGS. 1 and 2 respectively. According to FIGS. 1 and 2, the maximum absorption peak for the compound 2a appears at 275-400 nm, the maximum absorption peaks for the compounds 4ab, 4ad, 4ah, and 4aj appear at 340 nm, and the maximum absorption peak for the compound 4bf appears at 380 nm. If the compounds 2a, 4ab, 4ad, 4ah, 4aj, and 4bf were excited at the wavelengths of respective maximum absorption peaks, the compound 2a was not found to emit fluorescence, while the compounds 4ab, 4ad, 4ah, 4aj, and 4bf can emit orange-red fluorescence at 500-750 nm. These salts exhibit large Stokes shift orange-red fluorescence, which show possible application in OLED and bioimaging.

Although said descriptions and figures have disclosed preferable embodiments of the invention, it must be understood that possible applications of various additions, many modifications and replacements in preferable embodiments of the invention do not depart from the spirit and scope of the present invention which are as claimed by the appended claims. A person having ordinary skill in the art can realize that the invention can be used in various modifications in structure, arrangements, ratios, material, elements, and components. Therefore, the disclosed embodiments should be regarded as explanations of instead of limitations on the invention. The scope of the invention should be claimed by the appended claims and cover their legal equivalents, and should not be limited to the prior descriptions.

What is claimed is:

1. A 11-arylcinnolino[2,3-f]phenanthridinium salt compound having the structure of the following formula (F):

formula (F)

wherein CO₂Bu is butoxycarbonyl.

2. A 11-arylcinnolino[2,3-f]phenanthridinium salt compound having the structure of the following formula (G):

formula (G)

wherein R is selected from the group consisting of ester, amide, keto, carbocyclic aromatic, heteroaromatic, nitro, trifluoromethyl, phosphonate, phosphine oxide, sulfonyl, and sulfur oxide.

* * * * *